US007063969B2

(12) United States Patent
Smallridge et al.

(10) Patent No.: US 7,063,969 B2
(45) Date of Patent: Jun. 20, 2006

(54) YEAST-BASED PROCESS FOR PRODUCTION OF L-PAC

(75) Inventors: Andrew John Smallridge, Elwood (AU); Maurice Arthur Trewhella, Victoria (AU); Kylie Anne Wilkinson, Victoria (AU)

(73) Assignees: Victoria University of Technology, Victoria (AU); Polychip Pharmaceuticals Pty, Ltd., Victoria (AU)

( * ) Notice: Subject to any disclaimer, the term of this patent is extended or adjusted under 35 U.S.C. 154(b) by 95 days.

(21) Appl. No.: 10/149,821

(22) PCT Filed: Dec. 13, 2000

(86) PCT No.: PCT/AU00/01543

§ 371 (c)(1),
(2), (4) Date: Sep. 18, 2002

(87) PCT Pub. No.: WO01/44486

PCT Pub. Date: Jun. 21, 2001

(65) Prior Publication Data

US 2003/0077769 A1    Apr. 24, 2003

(30) Foreign Application Priority Data

Dec. 13, 1999    (AU) .................................. PQ4625

(51) Int. Cl.
*C12P 7/26* (2006.01)
*C12P 7/28* (2006.01)
(52) U.S. Cl. ...................... 435/148; 435/150; 435/156; 435/244; 435/255.2; 435/255.21; 435/171
(58) Field of Classification Search ................ 435/148, 435/150, 156, 244, 171, 255.21, 255.1, 255.2
See application file for complete search history.

(56) References Cited

U.S. PATENT DOCUMENTS

| 5,079,145 A | * | 1/1992 | Seely et al. .................... 435/34 |
| 5,173,413 A | | 12/1992 | Coughlin et al. |
| 5,306,637 A | * | 4/1994 | Lin et al. ..................... 435/259 |
| 6,271,008 B1 | * | 8/2001 | Smallridge et al. ......... 435/148 |

FOREIGN PATENT DOCUMENTS

| WO | WO 90/04639 | 5/1990 |
| WO | WO 99/63103 | 12/1999 |

OTHER PUBLICATIONS

Hudlicky et al., "Homochiral Amine Synthesis by Baker's Yeast Resolution of a β-Keto Amide: 1-Phenylethylamine," *Tetrahedron: Asymmetry* 3(2):281-286 (1992).
Sakaki et al., "Synthesis of 1,3-Dioxin-4-ones and Their Use in Synthesis. [1)] XVIII. Synthesis of Azetidin-2-ones From 1,3-Dioxin-4-ones via 3-Hydroxycarboxamides," *Chem. Pharm. Bull.* 37(11):2952-2960 (1989).
Nakamura et al., "Stereochemical Control in Microbial Reduction. XXI. Effect of Organic Solvents on Reduction of α-Keto Esters Mediated by Bakers' Yeast," *Bull. Chem. Soc. Jpn.* 66(9):2738-2743 (1993).
Kawai et al., "Yeast-Mediated Reduction of N-Substituted Acetoacetamides. Improvement of Conversion by Immobilization," *Bull. Chem. Soc. Jpn.* 61(8):3014-3016 (1998).
Isenschmid et al., "Effect of a Near-Critical and Supercritical Fluid on the Viability Ratio of Microbial Cells," *Biotechnol. Prog.*, 8 (Biocatalysis in Non-Conventional Media):407-416 (1992).
Bornemann et al., "Stereospecific Formation of R-Aromatic Acyloins by Zymomonas mobilis Pyruvate Decarboxylase,"*J. Chem. Soc., Perkin Trans 1*, pp. 425-430 (1995).
Cardillo et al., "Biotransformation of Unsaturated Aldehydes by Microorganisms with Pyruvate Decarboxylase Activity," *Appl. Microbiol. Biotechnol.* 36:300-303 (1991).
Kren et al., "Pyruvate Decarboxylase: A New Enzyme for the Production of Acyloins by Biotransformation," *J. Chem. Soc., Chem. Commun.*, pp. 341-343 (1993).
Chênevert et al., "Asymmetric Synthesis of Both Enantiomers of Fluoxetine via Microbiological Reduction of Ethyl Benzoylacetate," *Tetrahedron*, 33(48):6769-6776 (992).
Csuk & Glänzer, "Baker's Yeast Mediated Transformations in Organic Chemistry," *Chem. Rev.*, 91:49-97 (1991).
Grue-Sørensen & Spenser, "Biosynthesis of Ephedrine," *J. Am. Chem. Soc.*, 110:3714-3715 (1988).
Jayasinghe et al., "The Use of Organic Solvent Systems in the Yeast Mediated Reduction of Ethyl Acetoacetate," *Bull. Chem. Soc. Jpn.*, 67(9):2528-2531 (1994).
Jayasinghe et al., "The Yeast Mediated Reduction of Ethyl Acetoacetate in Petroleum Ether," *Tetrahedron Letters*, 34(24):3949-3950 (1993).

(Continued)

*Primary Examiner*—Irene Marx
(74) *Attorney, Agent, or Firm*—Klarquist Sparkman, LLP

(57) ABSTRACT

The invention provides a method of synthesis of a substituted or unsubstituted carbinol compound, comprising the steps of subjecting the corresponding substituted or unsubstituted aromatic aldehyde to acyloin condensation mediated by yeast in the presence of either (a) a supereritical fluid or (b) a liquefied gas, and recovering the carbinol compound. Preferably the yeast is *Saccharomyces cerevisiae*. In a particularly preferred embodiment the aromatic aldehyde is benzaldehyde and the carbinol is phenylacetylcarbinol, according to the reaction (I): in which the benzaldehyde, the pyruvic acid, or both may optionally be substituted.

7 Claims, No Drawings

OTHER PUBLICATIONS

Long et al., "Aromatic Aldehydes as Substrates for Yeast and Yeast Alcohol Dehydrogenase," *Biotechnology and Bioengineering*, 33:657-660 (1989).

Nakamura, "Stereochemical Control in Microbial Reduction. Part 10. Asymmetric Reduction of Alkyl 3-Methyl-2-Oxobutanoate With Immobilized Bakers' Yeast in Hexane," *Biocatalysis*, 3:17-24 (1990).

Nakamura et al., "Reduction by Bakers' Yeast in Benzene," *Tetrahedron Letters*, 32(48):7075-7078 (1991).

North, "Baker's Yeast Reduction of β-Keto Esters in Petrol," *Tetrahedron Letters*, 37(10):1699-1702 (1996).

Servi, "Baker's Yeast as a Reagent in Organic Synthesis," *Synthesis*, pp. 1-15 (1990).

Shin & Rogers, "Production of L-Phenylacetylcarbinol (L-PAC) from Benzaldehyde Using Partially Purified Pyruvate Decarboxylase (PDC)," *Biotechnology and Bioengineering*, 49:52-62 (1996).

* cited by examiner

YEAST-BASED PROCESS FOR PRODUCTION OF L-PAC

PRIORITY CLAIM

This is a U.S. National Stage § 371 application of PCT/AU00/01543, filed Dec. 13, 2000, which was published in English under PCT Article 21(2), which claims the benefit of Australian Application No. PQ 4625, filed Dec. 13, 1999.

This invention relates to organic compounds useful as precursors for the synthesis of a variety of products, particularly for synthesis of compounds useful as pharmaceutical agents. The method of the invention utilises yeast-mediated catalysis in the presence of a supercritical fluid or liquefied gas, and in particular the yeast-mediated condensation between pyruvate and a substituted aromatic aldehyde to yield the corresponding acyloin (hydroxy ketone) compound. In a preferred embodiment, the reaction is that between pyruvate and benzaldehyde to yield phenylacetylcarbinol, the precursor to ephedrine, in high enantiomeric purity.

BACKGROUND OF THE INVENTION

Physicochemical methods for production of enantiomerically pure compounds usually involve multi-step synthesis incorporating one or more steps which are asymmetric, and laborious purification procedures. Such methods are not only tedious, but frequently provide relatively poor yields. Alternatively enantiomerically-pure starting materials can be used, together with enantioselective reaction steps; however, such pure starting materials are available only for a very limited number of desired compounds.

In an attempt to overcome the difficulties of using traditional organic chemical methods, biological systems have been intensively investigated. Such systems show a very high degree of stereoselectivity in their reactions, and therefore microbiological, enzymatic or chemoenzymatic reactions for achieving specific reaction steps with a variety of reagents have been attempted. For example, microorganisms of a number of genera have been proposed for synthesis of optically active α-substituted derivatives of 3-hydroxypropionic acid for use as intermediates in the synthesis of compounds such as α-tocopherol, muscones and pharmaceutical, insecticidal and agricultural chemical agents (U.S. Pat. No. 4,734,367 by Hoffman-La Roche, Inc.). Most such procedures use whole-cell fermentation systems in aqueous media, or isolated enzymes with a specific desired activity. However, fermentation systems present the disadvantage that purification of the desired product can be difficult, and yields tend to be low; while the yield and convenience of the reaction can be improved by utilising immobilised cells, or cells which have been selected or genetically modified, this adds significantly to the cost of the process. The use of purified enzymes is normally prohibitively expensive, and again without the use of immobilised enzymes the yields tend to be low and purification difficult.

In recent years, intense efforts have been directed towards development of methods which are highly selective, provide a good rate of transformation, and enable easy, non-chromatographic separation and purification of the product. It would be particularly desirable if reactions could be carried out in organic solvents, since these are particularly convenient for large scale reactions and purifications.

It has been shown that dry baker's yeast is able to effect non-fermentative reduction of α-keto esters in organic solvents such as hexane or benzene, to produce the corresponding α-hydroxy esters with good yield and selectivity (Nakamura et al, 1988; Nakamura et al, 1990; Nakamura et al, 1991; Nakamura et al, 1993); reduction of β-keto esters in petroleum ether, diethyl ether, toluene, carbon tetrachloride and petrol has also been demonstrated (Jayasinghe et al, 1993; Jayasinghe et al, 1994; North, 1996). Although initially it was thought that immobilisation of yeast, for example in polyurethane, was essential in order to maintain stability of cell membrane-bound coenzymes for the dehydrogenases and reductases which catalyse the reaction (Nakamura et al, 1988; Nakamura et al, 1990), it was subsequently found that the addition of a very small proportion of water to the organic system would avoid the need for immobilisation (Nakamura et al, 1991).

Ephedrine (α-[1-(methylamino)ethyl]benzene-methanol), originally isolated from plants of the genus Ephedra, occurs as the naturally-occurring isomers l-ephedrine and d-pseudoephedrine, and other pharmacologically active isomers include d-ephedrine and l-pseudoephedrine. These compounds are adrenergic sympathomimetic agents and have antihistamine activity; l-ephedrine is widely used as a bronchodilator, while d-pseudoephedrine is widely used as a decongestant. Compounds of these groups are present in a very wide range of prescription and over-the-counter pharmaceutical formulations.

The production of l-phenylacetylcarbinol, a precursor of l-ephedrine, by catalysis using whole baker's yeast cells in aqueous medium was one of the first microbial biotransformation processes to be used commercially (Neuberg and Hirsch, 1921; see also Hildebrandt and Klavehn, 1934). This reaction involves the yeast-induced condensation of benzaldehyde with acetyl-coenzyme A. The reaction has been widely investigated, and has been shown to be mediated by the enzyme pyruvate decarboxylase (Groger, Schmander and Mothes, 1966). It has also been shown that the reaction has a relatively broad specificity for the substrate, enabling a variety of substituted aromatic aldehydes to be converted to the corresponding substituted optically-active phenylacetylcarbinols (Long, James and Ward, 1989).

Although this yeast-catalysed system has been widely exploited, this has normally utilised aqueous systems, which are inconvenient for large-scale extraction and purification, which require organic solvents. Additionally, fermentation systems present the disadvantage that purification of the desired product can be difficult, and yields tend to be low; while the yield and convenience of the reaction can be improved by utilising immobilised cells, or cells which have been selected or genetically modified, this adds significantly to the cost of the process. The use of purified enzymes is normally prohibitively expensive, and again without the use of immobilised enzymes the yields tend to be low and purification difficult.

In our earlier International Application PCT/AU99/00433, we showed that yeast-mediated acyloin condensation of benzaldehyde can be achieved in an organic solvent using non-fermenting yeast. The formation of side-products was suppressed by an addition of a small proportion of ethanol to the reaction mixture and by conducting the reaction at reduced temperature. When using organic solvents, there are problems with associated toxicity, occupational health and safety issues, flammability and waste disposal/recycling.

We have now surprisingly found that the yeast-mediated acyloin condensation of benzaldehyde can be achieved in supercritical or liquefied carbon dioxide or in liquefied petroleum gas. This reaction results in superior conversion of the aromatic aldehydes to the desired carbinol. In a preferred embodiment, yields of around 79% with the total absence of side-products were obtained using the method of the invention.

Even more surprisingly, it was found that carbon dioxide in either liquid or supercritical form deactivates the reduction reaction, thus inhibiting the formation of undesired side-products.

Since carbon dioxide is non-toxic and can be readily recycled, this method avoids the problems associated with reactions involving organic solvents.

Other supercritical fluids may be used, but may not prevent the formation of side-products without the addition of an inhibitor and may not have the same environmental advantages.

SUMMARY OF THE INVENTION

In a first aspect, the invention provides a method of synthesis of a substituted or unsubstituted carbinol compound, comprising the steps of subjecting the corresponding substituted or unsubstituted aromatic aldehyde to acyloin condensation mediated by yeast in the presence of either (a) a supercritical fluid, or (b) a liquefied gas, and recovering the carbinol compound.

Any yeast capable of effecting the acyloin condensation reaction may be used. It is economically advantageous to use the cheapest yeast available, and ordinary baker's yeast, *Saccharomyces cerevisiae*, is preferred. Strains of yeast adapted to other purposes, including brewing yeast and wine or sherry yeasts could also be employed. Strains specifically adapted to a supercritical fluid environment or for enhanced acyloin condensation efficiency may be used; such strains include conventionally-selected and genetically modified strains. For maximum efficiency of reaction, it is advisable to present the maximum surface area of yeast for contact with the reactants. This can be effected by using "active" dried yeast, which is readily commercially available as "instant dry yeast", and may be stored at room temperature. Alternatively, well-pulverised dry baker's yeast may be used. Other yeasts, such as those described in U.S. Pat. No. 4,734,367, or fungi such as those disclosed in Chênevert et al (1992) may also be used. The person skilled in the art will readily be able to test whether any specific organism will function for the purposes of the invention, using the methods described herein.

The supercritical fluid may be any suitable supercritical fluid with a critical temperature below 50° C. We have found that carbon dioxide is particularly suitable, as the reaction can be performed at a moderately elevated temperature, suitably between 33 to 42° C., preferably 35° C. At these temperatures, the corresponding pressure may range between 1500 to 2500 psi, preferably 1500 psi.

Other suitable supercritical fluids are known in the art, for example:

| Fluid | Critical temperature (° C.) | Critical pressure (psi) |
| --- | --- | --- |
| Ethane | 32.4 | 707.8 |
| Nitrous oxide | 36.6 | 1050 |
| Xenon | 16.7 | 847 |
| Fluoroform ($CHF_3$) | 26.3 | 705 |
| Monofluoromethane | 42 | 812.2 |
| Sulphur hexafluoride | 45.7 | 545.3 |
| Chlorotrifluoromethane | 29 | 561.3 |

When the condensation is performed in the presence of a supercritical fluid, the carbinol compound is recovered by subjecting the reaction mixture to extraction with a supercritical fluid or an organic solvent such as ethylacetate or diethylether.

The liquefied gas may be carbon dioxide, a hydrocarbon such as methane, ethane, propane, butane, ethylene, or the like, or mixtures thereof. Liquefied petroleum gas may be used.

The person skilled in the art will readily be able to test whether any specific supercritical fluid will function for the purposes of the invention, and to identify conditions of suitable temperature and pressure, using the methods described herein.

The person skilled in the art will also readily be able to determine whether a particular supercritical fluid or liquefied gas effectively inhibits the formation of side-products, or whether the addition of a suitable inhibitor is necessary. The use of ethanol as a suitable inhibitor is discussed in our International Application PCT/AU99/00433.

Once the yeast-mediated reaction has been completed, the system is de-gassed and the yeast extracted with either a supercritical fluid or an organic solvent.

In a preferred embodiment, the invention provides a method for yeast-mediated conversion of benzaldehyde to phenylacetylcarbinol, according to the following reaction:

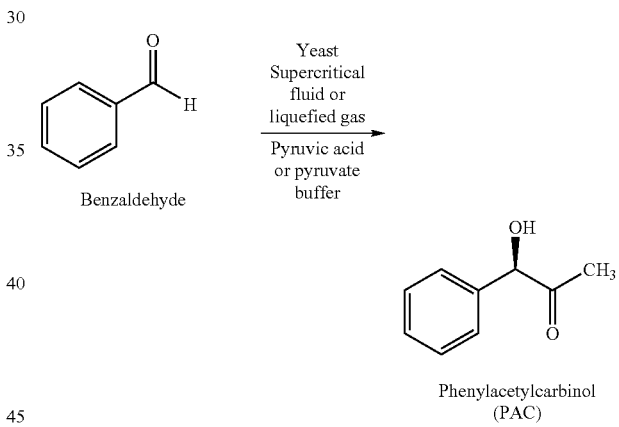

It will be clearly understood that the benzaldehyde, the pyruvic acid, or both may optionally be substituted, and that pyruvate, for example sodium pyruvate, may be used as an alternative to pyruvic acid. As a further alternative, a precursor of pyruvic acid which can be converted in situ to pyruvic acid may be used, for example, lactic acid, unless the supercritical fluid or liquefied gas is carbon dioxide. Aromatic aldehydes substituted with alkyl, aryl, halo, nitro, hydroxy, alkoxy, amino, carbonyl, thioxy or thioalkoxy groups or composites of these groups may also be used instead of benzaldehyde.

For either sodium pyruvate or pyruvic acid, the pH of the pyruvate/citrate buffer solution is preferably between 5 and 6, more preferably pH 6. Between 0.6 and 1.2 ml buffer/g of yeast should preferably be used for optimal results.

While the ratio of yeast to substrate will vary depending on the individual system, and is readily determined experimentally using routine trial and error methods, we have found that for the conversion of benzaldehyde to phenylacetylcarbinol the optimum ratio is 4.2 g yeast/mmol benzaldehyde; increasing the amount of yeast results in only a small increase in conversion, and lower amounts of yeast provide lower conversion.

Similarly, the optimum reaction time may readily be determined, and for the benzaldehyde-phenylacetyl-carbinol system we have investigated reaction times from 3 to 24 hours. Reactions longer than 24 hours do not lead to higher yields.

The reaction is significantly faster than prior art methods, even those using yeast. The supercritical fluid or liquefied gas used in the process can be recycled. The yeast can be used for other purposes, for example in animal feed, especially when this fluid or gas is carbon dioxide.

DETAILED DESCRIPTION OF THE INVENTION

The invention will now be described in detail by way of reference only to the following non-limiting examples.

EXAMPLE 1

Yeast-Mediated Acyloin Condensation of Benzaldehyde Using Sodium Pyruvate

Benzaldehyde (0.010 g, 0.1 mmol), sodium pyruvate (0.205 g), baker's yeast (0.415 g) and citrate buffer (0.415 ml, pH 6) was placed into a 15 ml stainless steel vessel. The vessel was pressurised to 2000 psi by pumping dried liquid carbon dioxide via a HPLC pump into the vessel and stirred in a 33° C. water bath for 24 hours. The reaction vessel was cooled after this time to room temperature and slowly de-gassed. The vessel contents and residue were washed 3 times with diethylether and filtered.

Gas chromatography analysis revealed that 82% of phenylacetylcarbinol had formed.

The mixture was purified using radial chromatography with petroleum ether:diethylether (70:30) to give pure l-PAC.

$[\alpha]_D = -377.7$ (c=0.006, CHCl$_3$)

$^1$H NMR (CDCl$_3$) δ7.30–7.55, m, Ph; δ5.15, s, CH; δ2.10, s, CH$_3$.

EXAMPLE 2

Yeast-Mediated Acyloin Condensation of Benzaldehyde Using Sodium Pyruvate

Benzaldehyde (0.010 g, 0.1 mmol), sodium pyruvate (0.205 g), baker's yeast (0.415 g) and citrate buffer (0.415 ml, pH 6) was placed into a 15 ml stainless steel vessel. The vessel was pressurised to 2000 psi by pumping dried liquid carbon dioxide via a HPLC pump into the vessel and stirred in a 33° C. water bath for 4 hours. The reaction vessel was cooled after this time to room temperature and slowly de-gassed. The vessel contents and residue were washed 3 times with diethylether and filtered.

Gas chromatography indicated a 62% conversion to phenylacetylcarbinol had formed.

The mixture was purified using radial chromatography with petroleum ether:diethylether (70:30) to give pure l-PAC.

$[\alpha]_D = -377.7$ (c=0.006 CHCl$_3$)

lit: $[\alpha]_D = -408.7$ (c=1.1 CHCl$_3$)

Takeshita, M. and Sato, T., Chem. Pharm. Bull. 1989 37 1085

$^1$H NMR (CDCl$_3$) δ7.30–7.55 m, Ph; δ5.15, s, CH; δ2.10, s, CH$_3$.

Conducting the above reaction at different temperatures and pressures for 4 hours gave the following conversions to l-PAC:

| Pressure → Temperature ↓ | 1500 psi | 2000 psi | 2500 psi |
|---|---|---|---|
| 33° C. | 63% | 62% | 38% |
| 35° C. | 68% | 45% | 79% |
| 38° C. | 47% | 41% | 76% |
| 42° C. | 10% | 12% | 36% |

EXAMPLE 3

Comparative Data

The following is a comparison of the supercritical fluid system (using carbon dioxide) with the organic solvent system disclosed in our earlier application.

|  | Supercritical fluid (CO$_2$) | Organic solvent |
|---|---|---|
| conversion | 79% | 32% |
| time | 4 hours | 24 hours |
| g yeast/mmol benzaldehyde | 4.2 | 5 |
| ml buffer/g yeast | 1 | 1 |
| g sodium pyruvate/mmol benzaldehyde | 2 | 2.5 |
| temperature | 35° C. | 5° C. |
| pressure | 2500 psi | N/A |

EXAMPLE 4

Reaction in Supercritical Carbon Dioxide

Benzaldehyde (0.137 g, 1.3 mmol), sodium pyruvate (2.168 g, 19.7 mmol), pH 6 citrate buffer (5.4 ml) and yeast (5.4 g) were placed into a 250 ml stainless steel pressure vessel. This vessel was pressurised to 1500 psi by pumping dried liquid carbon dioxide into the vessel. The vessel was then stirred in a 35° C. water bath for 3 h. After 3 h, the reaction vessel was cooled to room temperature and slowly de-gassed. The vessel contents and residue was washed three times with diethyl ether and filtered. Gas chromatography analysis revealed 84% conversion to phenylacetylcarbinol. Chiral gas chromatography (GC) showed a ratio of 87:13, 74% ee.

$^1$H NMR (CDCl$_3$) δ 7.30–7.55, m, Ph; δ 5.15, s, CH; δ 2.10, s, CH$_3$.

EXAMPLE 5

Reaction in Liquid Carbon Dioxide

Benzaldehyde (0.137 g, 1.3 mmol), sodium pyruvate (2.1685 g, 19.7 mmol), pH 6 citrate buffer (5.4 ml) and yeast (5.4 g) were placed into a 250 ml stainless steel pressure vessel. This vessel was pressurised to 1500 psi by pumping dried liquid carbon dioxide into the vessel. The vessel was then stirred at room temperature for 3 h. After 3 h, the reaction vessel was slowly de-gassed. The vessel contents and residue was washed three times with diethyl ether and filtered. Gas chromatography analysis revealed 84% conversion to phenylacetylcarbinol. Chiral GC showed a ratio of 95:5, 90% ee.

EXAMPLE 6

The Yeast-mediated Acyloin Condensation of Benzaldehyde Using Pyruvic Acid (a) Reaction in Supercritical Carbon Dioxide Benzaldehyde (0.137 g, 1.3 mmol), yeast (5.4 g) plus a mixture of pyruvic acid (0.216 g, 2.45 mmol) and water (5.4 ml), buffered to pH=5.45 using ammonium acetate, was placed into a 250 ml stainless steel pressure vessel. This vessel was pressurised to 1500 psi by pumping dried liquid carbon dioxide into the vessel. The vessel was then stirred in a 35° C. water bath for 3 h. After 3 h, the reaction vessel was cooled to room temperature and slowly de-gassed. The vessel contents and residue was washed three times with diethyl ether and filtered. Gas chromatography analysis revealed 44% conversion to phenylacetylcarbinol. Chiral GC showed a ratio of 96:4, 92% ee.

(b) Reaction in Liquid Carbon Dioxide

Benzaldehyde (0.137 g, 1.3 mmol), yeast (5.4 g) plus a mixture of pyruvic acid (0.216 g, 2.45 mmol) and water (5.4 ml), buffered to pH=5.45 using ammonium acetate, were placed into a 250 ml stainless steel pressure vessel. This vessel was pressurised to 1500 psi by pumping dried liquid carbon dioxide into the vessel. The vessel was then stirred at room temperature for 3 h. After 3 h, the reaction vessel was slowly de-gassed. The vessel contents and residue was washed three times with diethyl ether and filtered. Gas chromatography analysis revealed 51% conversion to phenylacetylcarbinol. Chiral GC showed a ratio of 97:3, 94% ee.

(c) Reaction in Liquefied Petroleum Gas

Benzaldehyde (0.137 g, 1.3 mmol), yeast (5.4 g) plus a mixture of pyruvic acid (0.216 g, 2.45 mmol) and water (5.4 ml), buffered to pH=5.45 using ammonium acetate, were placed into a 250 ml stainless steel pressure vessel. This vessel was pressurised to 100 psi using liquefied petroleum gas (LPG). The vessel was then stirred at room temperature for 24 h. After 24 h, the reaction vessel was slowly de-gassed. The vessel contents and residue was washed three times with diethyl ether and filtered. Gas chromatography analysis revealed 12% conversion to phenylacetylcarbinol.

(d) Reaction in Liquefied Petroleum Gas with the Addition of Ethanol

Benzaldehyde (0.137 g, 1.3 mmol, yeast (5.4 g), ethanol (0.54 ml) plus a mixture of pyruvic acid (0.216 g, 2.45 mmol) and water (5.4 ml), buffered to pH=5.45 using ammonium acetate, were placed into a 250 ml stainless steel pressure vessel. This vessel was pressurised to 100 psi using LPG. This vessel was then stirred at room temperature for 24 h. After 24 h, the reaction vessel was slowly de-gassed. The vessel contents and residue was washed three times with diethyl ether and filtered. Gas chromatography analysis revealed 14% conversion to phenylacetylcarbinol.

(e) Phenylacetylcarbinol Extraction Using Supercritical Carbon Dioxide

A typical reaction mixture obtained from the reaction in carbon dioxide was extracted using carbon dioxide at a pressure of 2009 psi and a temperature of 40° C. for a duration of 10 minutes. Subsequent gas chromatography analysis indicated that the phenylacetylcarbinol had been successfully isolated from the original reaction mixture.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Chênevert, R. Fortier, G. and Rhlid, R. B. Tetrahedron, 1992 48 6769–6776

Csuk, R. and Glänzer, B. I. Chem. Rev., 1991 91 49–57

Groger, D., Schmander, H. P. and Mothes, K. Z. Allg. Mikrobol., 1966 6 275

Hudlicky, T., Gillman, G. and Andersen, C. Tetrahedron Asymmetry, 1992 3 281

Jayasinghe, L. Y., Smallridge, A. J. and Trewhella, M. A. Tetrahedron Letters, 1993 34 3949

Jayasinghe, L. Y., Kodituwakku, D., Smallridge, A. J. and Trewhella, M. A. Bull. Chem. Soc. Jpn. 1994 67 2528

Kawai, A., Asano, T. and Imai, Y. Bull. Chem. Soc. Jpn., 1988 61 3014

Long, A., James, P. and Ward, O. P. Biotechnol. Bioeng., 1989 33 657–660

Nakamura, K., Inoue, K., Ushio, K., Oka, S. and Ohno, A. J. Org. Chem., 1988 53 2589–2593

Nakamura, K., Miyai, T., Inoue, K., Kawasaki, S., Oka, S. and Ohno, A. Biocatalysts, 1990 3 17–24

Nakamura, K., Kondo, S., Kawai, Y. and Ohno, A. Tetrahedron Letters, 1991 32 7075

Nakamura, K., Kondo, S., Kawai, Y. and Ohno, A. Bull. Chem. Soc. Jpn., 1993 66 2738

Neuberg, C. and Hirsch, J. Biochem. Z., 1921 115 282–310

North, M. Tetrahedron Letters, 1996 37 1699–1702

Sakaki, J., Kobayashi, S., Sato, M. and Kaneko, C. Chem. Pharm. Bull., 1989 37 2952–2961

Servi, S. Synthesis, 1990 1–25

Shiu, H. S. and Rogers, P. L. Biotechnol. Bioeng., 1996 49 52–62

The invention claimed is:

1. A method of synthesis of a carbinol compound, comprising subjecting benzaldehyde to acyloin condensation using *Saccharomyces* yeast in the presence of supercritical carbon dioxide at a reaction temperature of 33° C. to 42° C. and a reaction pressure of 1500 psi to 2500 psi, and recovering the carbinol compound.

2. The method of claim 1, wherein the ratio of yeast to benzaldehyde is 4.2 g/mmol.

3. The method of claim 2, wherein the benzaldehyde is converted to the carbinol in the presence of 0.6 to 1.2 ml of a buffer/g of yeast.

4. The method of claim 1, wherein the reaction temperature is maintained for 3 to 4 hours, then decreased to room temperature.

5. The method of claim 1, wherein the benzaldehyde is converted to the carbinol compound at a conversion rate of 41% or greater.

6. The method of claim 1, wherein the yeast comprises *Saccharomyces cerevisiae*.

7. A method of synthesis of a carbinol compound, comprising subjecting benzaldehyde to acyloin condensation using *Saccharomyces cerevisiae* yeast in the presence of supercritical carbon dioxide, sodium pyruvate, and a citrate buffer at a reaction temperature of 35° C. and a reaction pressure of 2500 psi, and recovering the carbinol compound.

* * * * *